United States Patent [19]

Simon et al.

[11] Patent Number: 5,917,039
[45] Date of Patent: Jun. 29, 1999

[54] N-ALKYLATION OF AMINES

[75] Inventors: Joachim Simon, Mannheim; Rainer Becker, Bad Dürkheim; Rolf Lebkücher, Mannheim; Horst Neuhauser, Dudenhofen, all of Germany

[73] Assignee: BASF Aktiengesellschaft, Ludwigshafen, Germany

[21] Appl. No.: 09/034,276

[22] Filed: Mar. 4, 1998

[30] Foreign Application Priority Data

Mar. 7, 1997 [DE] Germany ................................ 19709488

[51] Int. Cl.$^6$ ................................................. C07D 295/02
[52] U.S. Cl. .......................... 544/178; 546/184; 564/479
[58] Field of Search ........................ 544/178; 546/184; 564/479

[56] References Cited

U.S. PATENT DOCUMENTS

| 3,709,881 | 1/1973 | Warner . | |
| 4,647,664 | 3/1987 | Vanderpool et al. | 544/178 |
| 4,910,304 | 3/1990 | Fischer et al. | 544/178 |
| 5,847,131 | 12/1998 | Simon et al. | 544/178 |

FOREIGN PATENT DOCUMENTS

| 440829 | 8/1991 | European Pat. Off. . |
| 1106084 | 3/1968 | United Kingdom . |

OTHER PUBLICATIONS

*Chem. Abst.*, vol. 110, No. 9, Feb. 27, 1989 (HU 44479, Mar. 28, 1988).

*Pat. Abst. of Japan*, vol. 11, No. 163 (C–424), May 26, 1987 (JP 61 291551, Dec. 22, 1986).

*Pat. Abst. of Japan*, vol. 14, No. 485 (C–772), Oct. 23, 1990 (JP 02 202855, Aug. 10, 1990).

*Pat. Abst. of Japan*, vol. 2, No. 126 (C–025), Oct. 21, 1978 (JP 53 090227, Aug. 8, 1978).

*Primary Examiner*—Brian M. Burn
*Attorney, Agent, or Firm*—Keil & Weinkauf

[57] ABSTRACT

In a process for the N-alkylation of amines in which alcohols are reacted with alkylamines or dialkylamines in the presence of hydrogen, the reaction takes place on a catalyst based on copper and magnesium silicate and containing, in each case independently, 0 to 2% by weight of BaO, $Cr_2O_3$ and/or ZnO. The amines employed are mono- or dimethylamine or mono- or diethylamine, the alcohols employed are α,ω-diols, in particular diethylene glycol or pentanediol. In particular there is reaction of diethylene glycol with monomethylamine and/or monoethylamine to give N-methylmorpholine and/or N-ethylmorpholine.

9 Claims, No Drawings

N-ALKYLATION OF AMINES

The present invention relates to a process for the N-alkylation of amines in which alcohols are reacted with alkylamines or dialkylamines in the presence of hydrogen.

N-Methyl-substituted amines are normally prepared in the prior art by reacting alcohols with methylamine or dimethylamine on hydrogenating/dehydrogenating catalysts based on copper, nickel or cobalt under pressure at elevated temperatures.

GB-B-1 106 084 discloses the reaction of diethylene glycol with monomethylamine on a precipitated catalyst consisting of, for example, CuO/ZnO at from 150° C. to 400° C. under from 30 to 400 bar.

U.S. Pat. No. 3,709,881 discloses reacting diethylene glycol with methylamine on a nickel catalyst, such as nickel on kieselguhr, under 100 bar and at 225 to 250° C., resulting in N-methylmorpholine in a yield of 20 to 60%.

All the above processes are unsatisfactory in the range of applications and in the yields obtained.

Furthermore, EP-A-0 440 829 discloses the preparation of N-substituted cyclic amines from diols and alkylamines on a copper-containing precipitated catalyst consisting of copper on porous alumina and alumina hydrate in the presence of a catalytic amount of basic alkali metal or alkaline earth metal compounds. Although this process is able to meet industrial requirements in respect of the yield, the catalysts used in this case have a limited useful life and inadequate mechanical stability.

It is an object of the present invention to find an industrially and economically advantageous process for the N-alkylation of amines and to remedy the disadvantages of known processes.

We have found that this object is achieved by a process for N-alkylation in which alcohols are reacted with alkylamines or dialkylamines in the presence of hydrogen, the reaction taking place on a catalyst based on copper and magnesium silicate and comprising, in each case independently, 0 to 2% by weight of BaO, $Cr_2O_3$ and/or ZnO.

The alkyl radicals in the alkylamines or dialkylamines preferably have, independently, 1 to 6, particularly preferably 1 or 2, carbon atoms. Mono- or dimethylamine or mono- or diethylamine are particularly preferably employed.

The reaction in the process according to the invention, which is carried out continuously or batchwise, preferably continuously, is described for the example of methylamine or dimethylamine by the reaction equation detailed below.

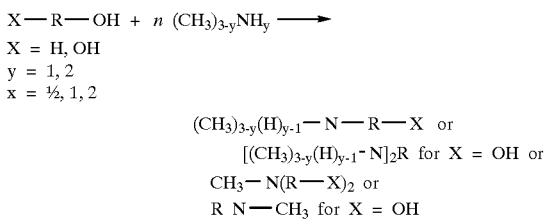

The reaction scheme also applies to the other alkylamines and dialkylamines detailed above. In these cases, R in the alcohol is an alkylene group preferably having 1 to 20, particularly preferably 3 to 14, in particular 4 to 7, specifically 5, carbon atoms, it being possible for the alkylene chain to be interrupted by 1 or 2 oxygen atoms, or, in particular, a group $-(CH_2)_p[-A-(CH_2)_m]_r$ with A=O, NH or $N-CH_3$, each of which can be unsubstituted or mono- or polysubstituted independently of one another by any suitable radicals such as $C_{1-6}$-alkyl radicals or halogen atoms, and m, p are, independently of one another, integers from 2 to 8 and r is 1, 2 or 3.

The alkyl and alkylene groups can be branched or unbranched. They are preferably unbranched. The alkylene group is preferably an α,ω-alkylene group. Alcohols generally suitable for this reaction have primary or secondary hydroxyl groups, and are preferably alkanols or alkanediols, very particularly α,ω-diols. Diethylene glycol or pentanediol is particularly preferably employed. The molar ratio of amine to alcohol in the process according to the invention is preferably 1:10 to 3:1, in particular 1.2:1 to 1.8:1.

In a preferred embodiment of the process according to the invention, the reaction is carried out in such a manner that the alcohols are reacted either in liquid phase under from 50 to 300 bar, preferably from 150 to 250 bar, particularly preferably about 200 bar at from 150 to 300° C., preferably 190 to 250° C., or in the gas phase under from 1 to 40 bar (absolute), preferably 15 to 35 bar (absolute), and at from 150 to 300° C., preferably 170 to 240° C., with mono- or dialkylamine.

The catalyst employed according to the invention is based on copper and magnesium silicate. Copper can moreover be present in metallic form or as copper oxide (CuO). The catalyst is preferably a precipitated catalyst or an unsupported catalyst. It thus contains a mixture of copper or copper oxide and magnesium silicate which is prepared, in particular, by joint precipitation from a copper-, magnesium- and silicate-containing solution. The content of copper in the form of CuO is preferably in the range from 30 to 60% by weight, particularly preferably 35 to 50% by weight. The copper or copper oxide can moreover be present on magnesium silicate as carrier.

The catalyst may, besides copper, also comprise other activating additives in the form of metal oxides, in each case independently, 0 to 2% by weight of BaO, $Cr_2O_3$ and/or ZnO. The preferred BaO content is from 0.1 to 2, in particular 0.5 to 1.5, % by weight. The $Cr_2O_3$ content is preferably 0.1 to 2, in particular 0.5 to 1.5, % by weight. The ZnO content is preferably 0.1 to 2, particularly preferably 0.3 to 1, % by weight. These % by weight are based on the total weight of the complete catalyst. The catalyst may furthermore comprise traces of other metals or metal oxides such as CaO, $Na_2O$ or $Fe_2O_3$.

The catalyst preferably employed is that marketed by BASF AG, Ludwigshafen, under the name R3-11. It contains about 45 to 47% by weight of CuO, magnesium silicate consisting of about 15 to 17% by weight of MgO and 35 to 36% by weight of $SiO_2$, about 0.9% by weight of $Cr_2O_3$, about 1% by weight of BaO and about 0.6% by weight of ZnO, plus traces of CaO, $Na_2O$ and $Fe_2O_3$.

The catalyst employed in the process according to the invention has, in a very particularly preferred embodiment, a BET surface area exceeding 100 $m^2/g$, in particular exceeding 200 $m^2/g$. The BET surface area is preferably 100 to 400 $m^2/g$, particularly preferably 200 to 400 $m^2/g$, in particular 250 to 350 $m^2/g$. The entire surface of the catalyst is moreover preferably covered with copper or copper oxide. The catalyst preferably has a porosity of from 0.2 to 0.7, particularly preferably 0.4 to 0.6, in particular about 0.5, ml/g.

The catalyst, in particular the unsupported catalyst, is mechanically stable under the abovementioned process conditions and shows no noticeable loss of activity over some weeks. This result is surprising inasmuch as it is known that finely dispersed copper is very severely attacked by ammonia and amines. The catalysts hitherto disclosed and employed for aminations accordingly contain only relatively little copper, if any, and have considerably smaller BET surface areas, markedly below 100 m²/g. Thus, for example, the BET surface area of the catalyst described in EP-A-0 440 829 is only 83 m²/g.

The catalyst is preferably employed as fixed bed in the form of beads, pellets, tablets, rings or other forms.

The space velocity is preferably in the range from 0.5 to 5, particularly preferably 1 to 3, kg of alcohol per kg of catalyst (calculated as kg of copper) and hour in a continuous procedure.

After the reaction, the products are isolated from the reaction mixture by conventional processes such as distillation or extraction. Unreacted starting materials are returned to the reaction where appropriate.

The invention also relates to the use of a catalyst as described above for the N-alkylation of amines.

The following examples serve to illustrate the process according to the invention in detail. The parts mentioned therein are parts by weight.

EXAMPLES

Preparation of the catalyst

Aqueous 20% by weight solutions of 90 parts of magnesium nitrate, 160 parts of copper (II) nitrate and 2 parts each of chromium (III) nitrate, barium nitrate and zinc nitrate are mixed together and then, while vigorously stirring at 20° C., an aqueous 15% by weight solution of 220 parts of potassium silicate is added. The resulting suspension is filtered with suction and then the filtered material is washed with water until the washings no longer contain nitrate ions. The filtered material is predried at 40° C. for 5 hours and then dried at 60° C. for a further 5 hours, calcined at 400° C. and shaped to tablets. The reductive treatment is initiated by heating the filtered material under a stream of nitrogen at 130° C. for one hour. The nitrogen is then gradually replaced over the course of 2 hours by hydrogen, increasing the temperature to 220° C. The catalyst is kept in a stream of pure hydrogen at 220° C. for a further 3 hours and then cooled. The catalyst prepared in this way has a BET surface area of 290 m²/g, a porosity of 0.51 ml/g and an apparent density of 0.9 kg/l.

Process examples

The reaction is carried out in a high-pressure reactor operated continuously under 200 bar. The oil-heated reactor consists of stainless steel and has a length of 170 cm and an internal diameter of 3 cm. During the reaction, 300 l(STP)/h of hydrogen are passed in addition to the amine and alcohol through the reactor. Downstream of the reactor, the product is condensed, decompressed and discharged in a conventional way.

Example 1

Preparation of N-methylmorpholine 160 g of monomethylamine and 420 g of diethylene glycol are passed per hour downwards through a bed of 700 ml of the catalyst prepared as above in the form of 5×3 mm tablets at 240° C. After 24 days, the diethylene glycol conversion is 98% and the N-methylmorpholine selectivity is 77%.

The catalyst shows no mechanical changes after removal.

Comparative Example 1

80 g of monomethylamine and 210 g of diethylene glycol are passed per hour downwards through a bed of 700 ml of the catalyst prepared as in the preparation example in EP-A 0 440 829 in the form of 5×3 mm tablets at 240° C. After 13 days, the diethylene glycol conversion is 94% and the N-methylmorpholine selectivity is 64%.

The catalyst after removal is found to be completely in the form of a red sludge.

Example 2

Preparation of N-methylpiperidine 160 g of monomethylamine and 420 g of pentanediol are passed per hour upwards through a bed of 700 ml of the catalyst prepared as above in the form of 5×3 mm tablets at 240° C. After 18 days, the pentanediol conversion is 99% and the N-methylpiperidine selectivity is 83%.

The catalyst shows no mechanical changes are removal.

Comparative Example 2

160 g of monomethylamine and 420 g of pentanediol are passed per hour upwards through a bed of 700 ml of the catalyst prepared as in the preparation example in EP-A 0 440 829 in the form of 5×3 mm tablets at 240° C. After 16 days, the pentanediol conversion is 99% and the N-methylpiperidine selectivity is 65%.

The catalyst after removal is found to be completely in the form of a red sludge.

Example 3

Preparation of N,N-dimethylethylamine 90 g of dimethylamine and 450 g of ethanol are passed per hour upwards through a bed of 700 ml of the catalyst prepared as above in the form of 5×3 mm tablets under 90 bar and at 200° C. After 2 days, the dimethylamine conversion is >95% and the N,N-dimethylethylamine selectivity is 80%.

The catalyst shows no mechanical changes after removal.

Comparative Example 3

90 g of dimethylamine and 450 g of ethanol are passed per hour upwards through a bed of 700 ml of the catalyst prepared as in the preparation example in EP-A 0 440 829 in the form of 5×3 mm tablets under 90 bar and at 200° C. After 2 days, the dimethylamine conversion is complete and the N,N-dimethylethylamine selectivity is 90%.

The catalyst after removal is found to be partly in the form of a red sludge.

We claim:

1. A process for N-alkylation of amines in which alcohols are reacted with alkylamines or dialkylamines in the presence of hydrogen, the reaction taking place on a catalyst based on copper and magnesium silicate and comprising, in each case independently, 0 to 2% by weight of BaO, $Cr_2O_3$ and/or ZnO.

2. A process as claimed in claim 1, where the catalyst comprises 30 to 60% by weight of CuO.

3. A process as claimed in claim 1, where the amines employed are mono- or dimethylamine or mono- or diethylamine.

4. A process as claimed in claim 1, where the alcohols employed are $\alpha,\omega$-diols, in particular diethylene glycol or pentanediol.

5. A process as claimed in claim 1, where diethylene glycol is reacted with monomethylamine and/or monoethylamine to give N-methylmorpholine and/or N-ethylmorpholine.

6. A process as claimed in claim 1, where pentanediol is reacted with monomethylamine and/or monoethylamine to give N-methylpiperidine and/or N-ethylpiperidine.

7. A process as claimed in claim 1, where the reaction is carried out in liquid phase under from 50 to 300 bar.

8. A process as claimed in claim 1, where the reaction is carried out in the gas phase under from 1 to 40 bar.

9. A process as claimed in claim 1, where the catalyst has a BET surface area of at least 100 $m^2/g$, preferably at least 200 $m^2/g$.

* * * * *